United States Patent [19]

Verdini et al.

[11] 4,439,360

[45] Mar. 27, 1984

[54] RETRO-INVERSO ANALOGUES OF C-TERMINAL PENTA AND HEXAPEPTIDES OF SUBSTANCE P

[75] Inventors: Antonio S. Verdini; Giuseppe C. Viscomi, both of Monterotondo, Italy

[73] Assignee: Anic S.p.A., Palermo, Italy

[21] Appl. No.: 448,832

[22] Filed: Dec. 10, 1982

[30] Foreign Application Priority Data

Dec. 22, 1981 [IT] Italy ............................... 25753 A/81

[51] Int. Cl.³ ..................... C07C 103/52; A61R 37/00
[52] U.S. Cl. ............................... 260/112.5 R; 424/177
[58] Field of Search .................. 260/112.5 R; 424/177

[56] References Cited

U.S. PATENT DOCUMENTS

3,862,114  1/1975  Scandrett ..................... 260/112.5 R

*Primary Examiner*—Delbert R. Phillips
*Attorney, Agent, or Firm*—Hedman, Gibson, Costigan & Hoare

[57] ABSTRACT

This invention relates to new retro-inverso peptides and peptide derivatives in the form of analogues and the C-terminal penta and hexapeptide fragments of Substance P, which are pharmacologically active, possess prolonged action with time and are useful as vasodilators, their general formula being:

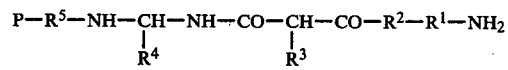

20 Claims, No Drawings

RETRO-INVERSO ANALOGUES OF C-TERMINAL PENTA AND HEXAPEPTIDES OF SUBSTANCE P

The undecapeptide Substance P, which is considered a neurotransmitter and a neuromodulator, is probably involved both in the neurotransmission of pain sensations and in the sensory axonal reflexes [Otsuka, M. and Takahashi, T., Annu. Rev. Pharmacol Toxicol, 17, 425 (1977); Henry, J. L., Brain Res., 114, 439 (1976); Celander, O. and Folkow, B., Acta Physiol. Scand., 29, 359 (1953); Narumi, S. and Maki, Y., J. Neurochem., 30, 1321 (1978); Oehme et al., Acta biol. med. germ., 39, 469 (1980), Haeusler, G. and Osterwalder, R., Naunyn-Schiemedeberg's Arch. Pharmacol., 314, 111 (1980); Hokfelt, T. et al. in "Substance P", Von Euler, U. S. and Pernow, B., Editors, Raven, New York, 1977, p. 117].

In the central nervous system, Substance P depolarises the neurons of the spinal medulla and stimulates or facilitates the response of the cells sensitive to pain stimuli [Konishi, S. and Otsuka, M., Brain Res. 65, 397 (1974); Henry, J. L. in "Substance P", Von Euler, U. S. and Pernow, B., Editors, Raven, New York, 1977, p. 231].

In the peripheral nervous system, Substance P, which possesses the property of contracting the smooth musculature and is one of the most powerful known vasodilators [Chernukh, A. M. et al., Exp. Biol. Med., 90, 1165 (1980); Lembeck, F. and Zetler, G., Int. Rev. Neurobiol., 4, 159 (1962); Schrauwen, E. et al., Pflungers Archiv. Eur. J. Physiol. 386, 281 (1980)].

All these activities of Substance P are also preserved in its C-terminal segments, in particular in the C-terminal hexa, hepta and octapeptide fragments [Blumdberg, S. and Teichberg, V. I., Biochem, Byophis. Res. Commun. 90, 347 (1979); Bury, R. W. and Mashford, M. L., J. Med. Chem. 19, 854 (1976); Otsuka, M. and Konishi, S. in "Substance P", Von Euler, U. S. and Pernow B., Editors, Raven, New York, 1977, p. 207; Rosell, S. et al. in Substance P, Von Euler, U. S. and Pernow B., Editors, Raven, New York, 1977, p. 83; Yanaihara, N. et al. in Substance P, Von Euler, U. S. and Pernow, B., Editors, Raven, New York, 1977, p. 27].

Structure-function studies carried out on a series of partial sequences and fragments of Substance P, prepared by chemical synthesis, have shown that the Substance P receptor interacts best with the natural hexa and heptapeptide C-terminal sequences, and that the extension of the chain beyond the C-terminal heptapeptide produces effects of negligible importance. Moreover, protecting the N-terminal residue by a tert-butyloxycarbonyl group significantly increases the power of the natural C-terminal pentapeptide, whereas it produces unimportant effects in longer peptides. [Teichberg, V. I. and Blumdberg, S., Prog. Biochem. Pharmacol. 16, 84 (1980); Chorev, M. et al., in "Peptides 1980", Proceedings of the 16th European Peptide Symposium, Brunfeldt, K., Scriptor, Copenhagen, 1981, p. 451].

It has also been shown that Substance P and its C-terminal hexa, hepta and octapeptide fragments are rapidly degraded by numerous proteolytic enzymes with endo and aminopeptidase activity [Gullbring, B., Acta Physiol. Scand. 6, 246 (1943); Teichberg, V. I. and Blumberg, S., Prog. Biochem. Pharmacol. 16, 84 (1980)].

The fact that Substance P and its C-terminal fragments are extremely labile towards enzymes makes their use problematical not only in characterisation studies of the Substance P receptor, but also their use in pharmacology. Attempts to stabilise the molecule, similar to those carried out successfully in the case of natural opioid peptides such as $Met^5$-Encephalin and $Leu^5$-Encephalin (substitution of Gly with D-Ala or substitution of aminoacid residues with N-methylaminoacid residues) have led to a substantial loss of power [Blumberg, S. and Teichberg, V. I., Biochem. Biophys. Res. Comm. 90, 347 (1979); Sandberg, B. E. B. et al., Eur. J. Biochem., 114, 329 (1981)].

In order to adequately protect the peptide sequence against the hydrolytic action of peptidase, we have now discovered, according to the present invention, that it is extremely advantageous to apply the criterion of retro-inversion of suitable peptide bonds to the C-terminal penta and hexapeptide fragments of Substance P.

We have therefore inverted one of the peptide bonds of the Substance P sequence which has proved most susceptible to the action of endopeptidase (the bond Phe-Gly), [Lee, C. M. et al., Eur. J. Biochem., 114, 315 (1981) and cited references], with the intention of making it more resistant to enzymatic degradation while preserving, by means of this modification, the three dimensional orientation of the peptide side chains, which is one of the indispensable requirements for maintaining the action power of the analogue. The inversion of a single peptide bond in the sequence requires the transformation of the two aminoacid residues used to form the inverted bond, and in particular the aminoacid residue closest to the amino end of the reference peptide, into a gem-diamino residue, and the transformation of the aminoacid residue closest to the carboxyl end into a residue of malonyl or 2-substituted malonyl type [Goodman, M. and Chorev, M., Acc. Chem. Res., 12, 1 (1979) and cited references].

While the incorporation of the malonyl or 2-substituted malonyl residues into the peptide skeleton does not present particular problems, the incorporation of the gem-diamino residues generally requires special and delicate synthesis manipulations [Goodman, M. and Chorev, M., in "Perspectives in Peptide Chemistry", Eberle, A., Geiger, R. and Wieland, T. Editors, Karger, Basel, 1980, p. 283].

We have considerably simplified the problem of introducing a gem-diamino residue into a peptide sequence by using the reagent I,I-bis(trifluoroacetoxy) iodobenzene as described in a copending patent application in the name of the same applicant. The reagent, the use of which is known in the direct conversion of primary carboxyl amides of simple structure into amines under extremely mild reaction conditions [Radhakrishna, A. S. et al., J. Org. Chem. 44, 1746 (1979)] is useful in the direct conversion of primary peptide and aminoacid amides, protected at the terminal $NH_2$, into the corresponding trifluoroacetic acid salts of N-monoacylated gem-diamino derivatives, as described in the said copending patent application. We have now discovered that which constitutes the subject matter of the present invention, namely that it is possible to synthesise two new classes of peptide analogues which are retro-inverted at the Phe-Gly bonds of the C-terminal penta and hexapeptide fragments of Substance P, by employing the results obtainable by using I,I-bis(trifluoroacetoxy) iodobenzene, in accordance with the process described in the said copending patent application.

The retro-inverso peptides according to the present invention are of general formula (I):

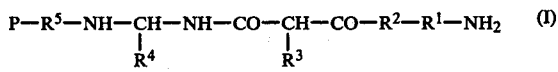

in which P is hydrogen, a linear or branched aliphatic alkyl group with 1-6 carbon atoms, or a saturated or unsaturated linear or branched chain aliphatic acyl group such as formyl, acetyl, propionyl, n-butyryl, isobutyrl, n-valeryl, isovaleryl, hexanoyl, isohexanoyl, heptanoyl, octanoyl, crotonoyl, methacryloyl, acryloyl; or a substituted acyl group such as hydroxyacetyl, 2-hydroxypropionyl, 3-hydroxypropionyl, aminoacetyl, 4-hydroxyphenylacetyl, 4-hydroxyphenylpropionyl, 2-aminopropionyl, 3-aminopropionyl, 0-ethylmalonyl, ethoxyformyl, methoxyacetyl, 3-methoxypropionyl, 3-ethoxypropionyl, chloroacetyl, dichloroacetyl, 2-chloropropionyl, 3-chloropropionyl, 2,3-dichloropropionyl, bromoacetyl, 4-hydroxy-3,5-diiodophenylacetyl, 3-oxobutyryl, 3-oxovaleryl, 4-oxovaleryl, methylthioacetyl, 3-methylthiopropionyl, ethylthioacetyl, 3-ethylthiopropionyl, nicotinoyl, γ-aminobutyryl, N$^\alpha$-[(1-(9-adenyl)-β-D-ribofuranuronosyl)], N$^\alpha$-[(1-9-hypoxanthyl)-β-D-ribofuranuronosyl)]; or a group such as benzyloxycarbonyl, tert-butyloxycarbonyl, tert-amyloxycarbonyl, isobornyloxycarbonyl, adamantyloxycarbonyl, chloro or nitro-substituted benzyloxycarbonyl; $R^1$ is a residue of methionine, methionine sulphoxide, methionine sulphone, selenomethionine, leucine, norleucine, valine or norvaline; $R^2$ is a residue of leucine, norleucine, valine, norvaline, alanine, isoleucine; $R^3$ is hydrogen or methyl; $R^4$ is the side-chain of aminoacids such as phenylalanine, tryptophan, tyrosine, valine, norvaline, leucine, norleucine, isoleucine, serine or derivatives, threonine or derivatives, histidine or derivatives, methionine, methionine-S-methyl, methionine sulphone, arginine or derivatives, lysine or derivatives, ornithine or derivatives, 2,4-diaminobutyric acid or derivatives, 2,3-diaminopropionic acid or derivatives, glutamic acid or aspartic acid or their suitable derivatives; $R^5$ is a peptide fragment containing 1 or 2 amino acid residues which constitute the quintultimate and sextultimate residue from the carboxyamide end, and of which the quintultimate can be phenylalanine, tyrosine, 4-chlorophenylalanine, 0-benzyltyrosine (or their acetyl, cyclopentyl, tert-butyloxycarbonyl or 4-hydroxyphenylacetyl derivatives) or glycine, and the sexultimate can be glutamine, pyroglutamic acid, alanine, tyrosine, lysine or derivatives, proline, N-formyl-proline, β-alanine, N-acetyl-β-alanine, glycine, desaminophenylalanine, desaminoglutamine, desaminoaspartic acid, methyldesaminoaspartic acid, or glutamic acid esters represented by general formula (II)

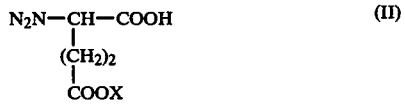

in which X is methyl, ethyl, methoxyethyl, methoxy (ethoxy)$_n$ ethyl where N=1, 2, 3, or their tert-butyloxycarbonyl derivatives.

In the synthesis descriptions reported hereinafter, use is made of the following abbreviations: Boc: tert-butyloxycarbonyl; OMe: methyl ester; DCC: NN'-dicyclohexylcarbodiimide; DMF: N,N-dimethylformamide; THF: tetrahydrofuran; NMH: N-methylmorpholine; MeOH: methanol; EtOH: ethanol; EtOAc: ethyl acetate; Et$_2$O: ethyl ether; HOBt: N-hydroxybenzothiazole; DCU: dicyclohexylurea; BTI: I.I-bis(trifluoroacetoxy) iodobenzene;

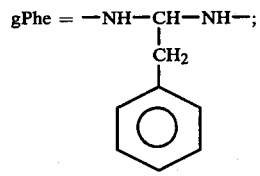

mGly=—OC—CH$_2$—CO—.

Each aminoacid is of L form, even if not expressly specified. A pentapeptide derivative of general formula (I) is synthesised by the condensation, generally induced by DCC+HOBt, of a N-monoacetylated gem-diamino residue of an aminoacid or peptide residue of which the terminal NH$_2$ has been conveniently protected, with a peptide fragment of general formula (III)

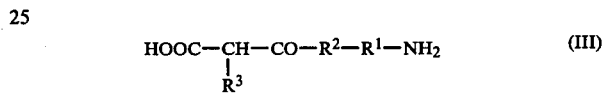

in which $R^3$, $R^2$ and $R^1$ have the same meaning as heretofore. A hexapeptide derivative of general formula (I) is synthesised by condensing a suitable aminoacid derivative at the pentapeptide fragment synthesised as described heretofore, and having its terminal NH$_2$ group free, using for this purpose the known condensation methods in peptide synthesis as described for example in Bodansky M. and Ondetti M., Peptide Synthesis Interscience, New York; 1966; Finn F. M. and Hoffmann K, The Proteins, vol. 2, Neurath A. and Hile R. L., Editors, Academic Press, New York, 1976; and The Peptides, vol. 1, Gross E. amd Meilnhofer J., Editors, Academic Press, New York, 1979.

After the reactions are complete, the peptides are obtained by known procedures in peptide isolation, such as extraction, counter-current distribution, precipitation, crystallisation and various types of chromatography.

The presence of the products was demonstrated by reverse phase high pressure chromatography analysis (RP—HPLC) using the following eluent systems: H$_2$O/acetonitrile; 0.01 M NH$_4$H$_2$PO$_4$/acetonitrile, 0.005 M heptanesulphonic acid, 0.01 M NH$_4$H$_2$PO$_4$/acetonitrile; and chromatography analysis on a thin silica gel layer using the following eluent systems: n.butanolacetic acid-water (4:1:1); chloroform-methanol-acetic acid 85:10:5); n.butanol-isopropanol 1 N NH$_4$OH-ethyl acetate (1:1:5:1) (organic phase).

The melting points have not been corrected.

The pharmacological activity of the retro-inverso analogues according to the present invention was tested by measuring the contraction of the isolated ileum of the guinea pig, as described by Rossel and colleagues (Rossel S. et al., in "Substance P", Von Euler, V. S. and Pernow B., Editors, Raven, New York 1977, p. 83) and by measuring the increase in the flow of K$^+$ ions from testpieces of the parotidean tissue of the rat, as described by Rudich and Butcher [Rudich L. and Butcher F. R., Biochim Biophys. Acta. 444, 704 (1976)], with reference to the activity of the peptide

[<(Glu⁶)]SP₆₋₁₁

The table shows the results of the pharmacological tests carried out using the analogue

[<Glu⁶,gPhe⁸,mGly⁹]SP₆₋₁₁

TABLE 1

| Analogues of C-terminal hexapeptides of Substance P | Guinea pig ileum contraction (%) | K⁺ release by parotidean tissue (%) | Duration of action (in minutes) |
|---|---|---|---|
| [<Glu⁶]SP₆₋₁₁ | 100 | 100 | 20 |
| [<Glu⁶, gPhe⁸, mGly⁹]SP₆₋₁₁ | 15 | 10 | No decrease (20 hours) |

The subject matter and scope of the invention will be more apparent on reading the following example, which is merely illustrative and must in no way be considered as limitative of the invention.

EXAMPLE

Synthesis of pyroglutamylphenylalanylgemdiaminophenylalanyl-malonylleucylmethionineamide.
Pyr-PhegPhe-mGly-Leu-Met-NH2 Synthesis of tert-butyloxycarbonylleucylmethionine methyl ester.
Boc-Leu-Met-OMe 1.0 equivalents of Boc-Leu are dissolved in anhydrous THF, and 1.0 equivalents of N.M.M. and 1.1 equivalents of isobutylchloroformate are added to the solution, which is cooled to $-15°$ C. and maintained in a nitrogen atmosphere.

After two minutes, a solution prepared by dissolving 1.0 equivalents of HCl.Met-OMe and 1.0 equivalents of N.M.M. in DMF is added.

During the additions, the temperature is checked to ensure that it does not exceed $-10°$ C. Having verified the disappearance of HCl.Met-OMe, the reaction is suspended by evaporating the mixture to dryness, the residue is taken up in EtOAc and washed with a 5% sodium bicarbonate solution, water, a 5% citric acid solution, and water.

The solution of EtOAc is then dried over magnesium sulphate, and the product is obtained by crystallisation, by suitably adding 30°–50° C. petroleum ether. M.P.=102°–104° C.

$[\alpha]_{22}^{589} = -36.1°$ (C=1.0 in DMF).

Elementary analysis for $C_{17}H_{32}N_2O_5S$: Theoretical: C, 54.23%; H, 8.57%; N, 7.44%. Found: C, 54.10%; H, 8.49%; N, 7.39%.

Chromatography analysis (thin layer chromatography and HPLC) shows no presence of impurities, and the ¹H n.m.r. spectrum confirms the molecular structure.

Synthesis of tert-butyloxycarbonylleucylmethionineamide.
Boc-Leu-Met-NH₂

1.0 equivalents of Boc-Leu-Met-OMe are dissolved in anhydrous MeOH, and anhydrous ammonia is passed for 30 minutes into this solution, cooled to $-5°$.

The solution, contained in a hermetically sealed vessel, is kept overnight at ambient temperature, after which the product is obtained in crystalline form by adding a volume of water equal to about 30% of the volume of MeOH. M.P.=158°–160° C.

$[\alpha]_{22}^{589} = -35.4°$ (C=1 in DMF).

Elementary analysis for $C_{16}H_{31}N_3O_4S$: Theoretical: C, 53.16%; H, 7.33%; N, 11.63%. Found: C, 53.03%; H, 7.23%; N, 11.50%.

Chromatography analysis (thin layer chromatography and HPLC) shows no presence of impurities, and the ¹H n.m.r. spectrum confirms the molecular structure.

Synthesis of leucylmethionineamide hydrochloride.HCl.Leu-Met-NH₂

1.0 equivalents of Boc-Leu-Met-NH₂ are dissolved in 10 ml of a 4.5 M solution of HCl in EtOAc.

Having verified the disappearance of the starting substance, the reaction solvent is evaporated to dryness, the residue taken up with MeOH and crystallised by suitably adding Et₂O.

M.P.=125°–127° C.

$[\alpha]_{22}^{589} = 10.5$ (C=1.0 in H₂O).

Elementary analysis for $C_{11}H_{24}N_3O_2$ S.Cl.CH₃OH: Theoretical: C, 43.70%; H, 8.55%; N, 12.73%. Found: C, 43.55%; H, 8.42%; N, 12.63%.

The ¹H n.m.r. spectrum confirms the molecular structure. The product is pure, this having been verified by chromatography analysis (t.l.c. and HPLC).

Synthesis of malonylleucylmethioneamide methylester
(CH₃)O-mGly-Leu-Met-NH₂

1.0 equivalents of methyl monomalonate are dissolved in CH₂Cl₂, the solution is cooled to 0° C., after which 1.5 equivalents of HOBt dissolved in DMF and 1.1 equivalents of DCC dissolved in CH₂Cl₂ are added to it. After 20 minutes, 1.0 equivalents of HCl.Leu-Met-NH₂ are added to the cold mixture, followed by 1.1 equivalents of N.M.M. The ice bath is removed after about one hour, and having verified the disappearance of the hydrochloride the reaction mixture is filtered, the precipitated dicyclohexylurea is washed with portions of THF, and the resultant solution and wash liquors evaporated to dryness. The residue obtained is washed with small volumes of 5% sodium bicarbonate, water, 5% citric acid and water, and is then dried over P₂O₅. The product is crystallised from DMF/Et₂O.

M.P.=184°–185° C.

$[\alpha]_{22}^{589} = -33.6$ (C=0.87 in DMF)

Elementary analysis for $C_{15}H_{27}N_3O_5S$: Theoretical: C, 49.86%; H, 7.48; N, 11.63%. Found: C, 49.75%; H, 7.43%, N, 11.60%

Chromatography analysis (t.l.c. and HPLC) shows no presence of impurities, and the ¹H n.m.r. spectrum confirms the molecular structure.

Synthesis of malonylleucylmethionineamide
mGly-Leu-Met-NH₂

1.0 equivalents of (CH₃)O-mGly-Leu-Met-NH₂ are dissolved in MeOH, and 3 equivalents of a 3 M aqueous solution of NaOH are added to the solution.

Having verified the disappearance of the starting ester, the methanol is diluted with water, then eliminated, and the residual solution acidified to pH 2 with concentrated HCl, then extracted repeatedly with EtOAc. The extracts are combined, dried with magnesium sulphate and evaporated to dryness. The product is crystallised from dioxane/30°–50° C. petroleum ether. M.P.=136°–138° C. (dec.).

$[\alpha]_{22}^{589} = -38.9$ (C=1.3 in DMF).

Elementary analysis for $C_{14}H_{25}N_3O_5S$: Theor: C, 48.14%; H, 7.20%; N, 12.10%. Found: C, 47.12%; H, 7.91%; N, 12.00%.

Chromatography analysis (t.l.c. and HPLC) shows no presence of impurities, and the $^1H$ n.m.r. spectrum confirms the molecular structure.

Synthesis of tert-butyloxycarbonyl-phenylalanylphenylalanine methylester.Boc-Phe-Phe-Ome 1.0 equivalents of Boc-Phe are dissolved in anhydrous THF, after which 1.0 equivalents of N.M.M. and 1.1 equivalents of isobutylchloroformate are added to the solution cooled to −15° C. and kept under a nitrogen atmosphere. After 2 minutes, a solution prepared by dissolving 1.0 equivalents of HCl.Phe-OMe and 1.0 equivalents of N.M.M. in DMF is added. During the addition of the isobutylchloroformate and HCL. Phe-OMe, the temperature is checked to ensure that it does not exceed −10° C.

Having verified the disappearance of HCl.Phe-OMe, the reaction is suspended by evaporating the solvent mixture to dryness, the residue is taken up in EtOAc and washed with 5% sodium bicarbonate solution, water, 5% citric acid solution and water. The EtOAc solution is dried over magnesium sulphate, and the product is obtained in crystalline form by adding 30°–50° petroleum ether. M.P.=121°–123° C.

$[\alpha]_{22}^{589} = 5.5°$ (C=1.0 in acetic acid).

Elementary analysis for $C_{24}H_{30}N_2O_5$: Theoretical: C, 67.58%; H, 7.09%; N, 6.57%. Found: C, 67.49%; H, 6.99%; N, 6.78%.

Chromatography analysis (t.l.c. and HPLC) shows no presence of impurities, and the $^1H$ n.m.r. spectrum confirms the molecular structure.

Synthesis of tert-butyloxycarbonylphenylalanylphenylalanylamide. Boc-Phe-Phe-NH₂

1.0 equivalents of Boc-Phe-Phe-OMe are dissolved firstly in DMF and then diluted with MeOH.

Anhydrous ammonia is passed for 30 minutes through the solution cooled to −5° C. Having interrupted the flow of ammonia, after about 1 hour, the solution is kept in a hermetically sealed vessel overnight at ambient temperature. The required product, which is obtained by adding an excess of water after evaporating the MeOH, is filtered, dried over $P_2O_5$ under vacuum, and collected. M.P.=208°–210° C.

$[\alpha]_{22}^{589} = -24.5°$ (C=1.0 in DMF).

Elementary analysis for $C_{23}H_{25}N_3O_4$: Theoretical: C, 67.15%, H, 7.06%; N, 10.22%. Found: C, 67.00; H, 6.99%; N, 10.15%

Chromatography analysis (t.l.c. and HPLC) shows no presence of impurities, and the $^1H$ n.m.r. spectrum confirms the molecular structure.

Synthesis of tert-butyloxycarbonylalanylphenylphenylalanylgem-diaminophenylalamine hydrochloride. BOC-Phe-g Phe HCl 1.0 equivalents of Boc-Phe-Phe-NH₂ are suspended in a 3:2 (v/v) acetonitrile:water mixture, and 1.2 equivalents of BTI dissolved in acetonitrile are added to the solution at ambient temperature under vigorous stirring.

An inert gas is bubbled through the reaction mixture in order to facilitate removal of the $CO_2$ developed during the reaction. Having verified the disappearance of Boc-Phe-Phe-NH₂, the reaction is suspended by evaporating to dryness 5 hours after adding the reagent, the residue is washed with ethyl ether, dried and dissolved in EtOH. The stoichiometric quantity of HCl dissolved in EtOAc is added to this solution to induce complete precipitation of Boc-Phe-gPhe- HCl over a period of 2 hours. The precipitate is filtered, washed abundantly with various portions of ethyl ether, dried over $P_2O_5$ under vacuum, and collected. M.P.=174° C. (dec.).

$[\alpha]_{22}^{589} = -48.8°$ (C=1.0 in DMF).

Elementary analysis for $C_{22}H_{30}O_3N_3Cl$: Theoretical: C, 62.94%; H, 7.15%; N, 10.01%. Found: C, 62.39%; H, 7.12%; N, 10.27%.

Chromatography analysis (t.l.c. and HPLC) shows no presence of impurities and the $^1H$ n.m.r. spectrum confirms the molecular structure.

Synthesis of tert-butyloxycarbonyl-phenylalanylgem-diamino-phenylalanylmalonyl-leucylmethionineamide. Boc-Phe-gPhe-mGly-Leu-Met-NH₂

1.0 equivalents of mGly-Leu-Met-NH₂ are dissolved in THF, the solution is cooled to 0° C., after which 1.5 equivalents of HOBt dissolved in DMF and 1.1 equivalents of DCC dissolved in THF are added to the solution. After 20 minutes, 1.0 equivalents of Boc-Phe-gPhe- HCl and 1.1 equivalents of N.M.M. are added to the cold mixture.

The ice bath is removed after about 1 hour, and the mixture is left to react overnight at ambient temperature.

After filtering off the dicyclohexylurea precipitate, which is washed with THF, the solution and wash liquors are reduced to about 10 ml, and a white flaky precipitate is obtained by subsequent treatment with an excess of water. The precipitate is filtered, washed with numerous portions of a 5% citric acid solution, water, a 5% sodium bicarbonate solution and water. After drying over $P_2O_5$ under vacuum, the solid residue is further washed with $Et_2O$, dried and collected. M.P.=242°–243° C.

$[\alpha]_{22}^{589} = -12.33$ (C=10.7 in DMF).

Elementary analysis for $C_{36}H_{52}N_6O_7S$: Theoretical: C, 60.67%; H, 7.30%; N, 11.80%. Found: C, 60.60%; H, 7.09%; N, 11.69%.

Analysis of aminoacids: Theoretical: Phe, 1.00; Leu, 1.00; Met, 1.00. Found: Phe, 1.03; Leu, 1.00; Met, 0.87.

Chromatography analysis (t.l.c. and HPLC) shows no presence of impurities, and the $^1H$ n.m.r. spectrum confirms the molecular structure.

Synthesis of phenylalanyl-gemdiaminophenylalanylmalonylleucyl-methionineamide hydrochloride.
HCl.Phe-gPhe-mGly-Leu-Met-NH$_2$ 1.0 equivalents of Boc-Phe-gPhe-mGly-Leu-Met-NH$_2$ are dissolved in 15 ml of a 4.5 M solution of HCl in EtOAc. Having verified the disappearance of the starting substance, the reaction solvent is evaporated to dryness, the residue taken up in DMF and crystallised by adding a suitable quantity of Et$_2$O.

M.P.=236°–238° C.

$[\alpha]_{22}^{589} = -10.2$ (C=1.0 in DMF).

Elementary analysis for C$_{31}$H$_{45}$N$_6$O$_5$SCl Theoretical: C, 57.37%; H, 6.94%; N, 12.95%. Found: C, 57.30%; H, 6.80%; N, 12.88%.

Chromatography analysis (t.l.c. and HPLC) shows no presence of impurities, and the $^1$H n.m.r. spectrum confirms the molecular structure.

Synthesis of pyroglutamylphenylalanylgemdiaminophenylalanyl-malonylleucylmethionineamide.
Pyr-Phe-gPhe-mGly-Leu-Met-NH$_2$ 1.0 equivalents of pyroglutamic acid are dissolved in DMF and the solution is cooled to 0° C., after which 1.5 equivalents of HOBc dissolved in DMF and 1.1 equivalents of DCC dissolved in THF are added. After 20 minutes, 1.0 equivalents of HCl.Phe-gPhe-mGly-Leu-Met-NH$_2$ and 1.1 equivalents of N.M.M. are added. The ice bath is removed after about 1 hour, and the mixture is left to react overnight at ambient temperature. Having verified the disappearance of HCl.Phe-gPhe-mGly-Leu-Met-NH$_2$, the solution is filtered, and the dicyclohexylurea precipitate is washed with THF. The resultant solution and the wash liquors are reduced to a small volume, and a flaky precipitate is obtained by treatment with an excess of water. The required product is isolated by reverse phase high pressure preparative liquid chromatography, the stationary phase consisting of Lichroprep 25.40 μm (Merck), and using H$_2$O/CH$_3$Cn 20% as eluent. The product is recovered by lyophilisation after evaporating the acetonitrile.

M.P.=261°–265° C.

$[\alpha]_{22}^{546} = -10.0$ (C=0.5 in DMF).

Elementary analysis for C$_{36}$H$_{49}$N$_7$O$_7$S: Theoretical: C, 59.75%; H, 6.77%; N, 13.55%. Found: C, 59.67%; H, 6.69%; N, 13.49%.

Analysis of aminoacids: Theoretical: Gln, 1.00; Phe, 1.00; Leu, 1.00; Met, 1.00. Found: Gln, 1.04; Phe, 1.00; Leu, 1.00; Met, 0.93.

Chromatography analysis (t.l.c. and HPLC) shows no presence of impurities, and the $^1$H n.m.r. spectrum confirms the molecular structure.

We claim:

1. Compounds of general formula (I):

$$P-R^5-NH-\underset{R^4}{CH}-NH-CO-\underset{R^3}{CH}-CO-R^2-R^1-NH_2 \quad (I)$$

in which

P is hydrogen, a linear or branched aliphatic alkyl group of 1–6 carbon atoms, or a saturated or unsaturated linear or branched chain aliphtic acyl group, such as formyl, acetyl, propionyl, n-butyryl, isobutyryl, n-valeryl, isovaleryl, hexanoyl, isohexanoyl, heptanoyl, octanoyl, crotonoyl, methacryloyl, acryloyl; or a substituted acyl group such as hydroxyacetyl, 2-hydroxypropionyl, 3-hydroxypropionyl, aminoacetyl, 4-hydroxyphenylacetyl, 4-hydroxyphenylpropionyl, 2-aminopropionyl, 3-aminopropionyl, 0-ethylmalonyl, ethoxyformyl, methoxyacetyl, 3-methoxypropionyl, 3-ethoxypropionyl, chloroacetyl, dichloroacetyl, 2-chloropropionyl, 3-chloropropionyl, 2,3-dichloropropionyl, bromoacetyl, 4-hydroxy-3,5-diiodophenylacetyl, 3-oxobutyryl, 3-oxovaleryl, 4-oxovaleryl, methylthioacetyl, 3-methylthiopropionyl, ethylthioacetyl, 3-ethylthiopropionyl, nicotinoyl, γ aminobutyryl, N$^\alpha$-[1-(9-adenyl)-β-D-ribofuranuronosyl], N$^\alpha$-[1-(9-hypoxanthyl)-β-D-ribofuranuronosyl]; or a group such as benzyloxycarbonyl, tert-butyloxycarbonyl, tert-amyloxycarbonyl, isobornyloxycarbonyl, adamantyloxycarbonyl, chloro or nitro-substituted benzyloxycarbonyl;

R$^1$ is a residue of methionine sulphoxide, methionine sulphone, selenomethionine, leucine, norleucine, valine or norvaline;

R$^2$ is a residue of leucine, norleucine, valine, norvaline, alanine or isoleucine;

R$^3$ is hydrogen or methyl;

R$^4$ is the side-chain of aminoacids such as phenylalanine, tryptophan, tyrosine, valine, norvaline, leucine, norleucine, isoleucine, serine or derivatives, threonine or derivatives, histidine or derivatives, methionine, S-methyl methionine, methionine sulphone, arginine or derivatives, lysine or derivatives, ornithine or derivatives, 2,4-diaminobutyric acid or derivatives, 2,3-diaminopropionic acid or derivatives, glutamic acid or aspartic acid or their suitable derivatives;

R$^5$ is a peptide fragment containing 1 or 2 aminoacid residues which constitutes the quintultimate and sextultimate residue from the carboxyamide end, and of which the quintultimate can be: phenylalanine, tyrosine, 4-chlorophenylalanine, 0-benzyl-tyrosine (or their acetyl, cyclopentyl, tert-butyloxycarbonyl or 4-hydroxyphenylacetyl derivatives) or glycine; and the sextultimate can be: glutamine, pyroglutamic acid, alanine, tyrosine, lysine or derivatives, proline, N-formyl-proline, β-alanine, N-acetyl-β-alanine, glycine, desaminophenylalanine, desaminoglutamine, desaminoaspartic acid, γ-methyldesaminoaspartic acid, or γ-esters of glutamic acid represented by the general formula (II)

$$\begin{array}{c} H_2N-CH-COOH \\ | \\ (CH_2)_2 \\ | \\ COOX \end{array}$$

in which X is methyl, ethyl, methoxyethyl, methoxy (ethoxy)$_n$ ethyl where n=1, 2, 3, or their tert-butyloxycarbonyl derivatives.

2. A peptide as claimed in claim 1, constituted by 5 or 6 aminoacid residues.

3. The peptide Boc-Phe-gPhe-mGly-Leu-Met-NH$_2$ in which all the aminoacids are of L configuration.

4. The peptide Boc-Phe-gPhe-(R,S)mAla-Leu-Met-NH$_2$ in which all the aminoacids are of L configuration.

5. The peptide cyclopentyl-Phe-gPhe-mGly-Leu-Met-NH$_2$ in which all the aminoacids are of L configuration.

6. The peptide cyclopentyl-Phe-gPhe-(R,S)mAla-Leu-Met-$NH_2$ in which all the aminoacids are of L configuration.

7. The peptide Pyr-Phe-gPhe-mGly-Leu-Met-$NH_2$ in which all the aminoacids are of L configuration.

8. The peptide Pyr-Phe-gPhe-(R,S)mAla-Leu-Met-$NH_2$ in which all the aminoacids are of L configuration.

9. The peptide HCO-Pro-Phe-gPhe-mGly-Leu-Met-$NH_2$ in which all the aminoacids are of L configuration.

10. The peptide HCO-Pro-Phe-gPhe-(R,S)mAla-Leu-Met-$NH_2$ in which all the aminoacids are of L configuration.

11. The peptide Boc-Pro-Phe-gPhe-mGly-Leu-Met-$NH_2$ in which all the aminoacids are of L configuration.

12. The peptide Boc-Pro-Phe-gPhe-(R,S)mAla-Leu-Met-$NH_2$ in which all the aminoacids are of L configuration.

13. The peptide cyclopentyl-Pro-Phe-gPhe-mGly-Leu-Met-$NH_2$ in which all the aminoacids are of L configuration.

14. The peptide cyclopentyl-Pro-Phe-gPhe-(R,S)mAla-Leu-Met-$NH_2$ in which all the aminoacids are of L configuration.

15. The peptide cyclopentyl-Gln-Phe-gPhe-mGly-Leu-Met-$NH_2$ in which all the aminoacids are of L configuration.

16. The peptide cyclopentyl-Gln-Phe-gPhe-(R,S)mAla-Leu-Met-$NH_2$ in which all the aminoacids are of L configuration.

17. The peptide Pyr-Phe-gPhe-mGly-Leu-Met(O)-$NH_2$ in which all the aminoacids are of L configuration.

18. The peptide Pyr-Phe-gPhe-(R,S)mAla-Leu-Met-(O)-$NH_2$ in which all the aminoacids are of L configuration.

19. The peptide Pyr-Phe-gPhe-mGly-Leu-Met(-S=O)-$NH_2$ in which all the aminoacids are of L configuration.

20. The peptide Pyr-Phe-gPhe-(R,S)mAla-Leu-Met(-S=O)-$NH_2$ in which all the aminoacids are of L configuration.

* * * * *